US006823216B1

(12) United States Patent
Salomir et al.

(10) Patent No.: US 6,823,216 B1
(45) Date of Patent: Nov. 23, 2004

(54) SET FOR HEAT TREATMENT OF BIOLOGICAL TISSUES AND METHOD USING SAME

(75) Inventors: Rares-Vasile Salomir, Bordeaux (FR); Jacobus Adrianus de Zwart, Bordeaux (FR); Frédéric Vimeux, Bordeaux (FR); Christ Moonen, Gradignan (FR)

(73) Assignee: Centre National de la Recherche Scientifique (CNRS), Paris Cedex (FR)

(*) Notice: Subject to any disclaimer, the term of this patent is extended or adjusted under 35 U.S.C. 154(b) by 25 days.

(21) Appl. No.: 10/070,929

(22) PCT Filed: Sep. 12, 2000

(86) PCT No.: PCT/FR00/02506

§ 371 (c)(1),
(2), (4) Date: Jun. 26, 2002

(87) PCT Pub. No.: WO01/19457

PCT Pub. Date: Mar. 22, 2001

(30) Foreign Application Priority Data

Sep. 13, 1999 (FR) ............................................ 99 11418

(51) Int. Cl.[7] .................................................. A61F 2/00
(52) U.S. Cl. ........................... 607/101; 607/102; 601/2; 600/411
(58) Field of Search ................................ 607/101–105, 607/97–99, 96; 606/27–29; 601/2, 2.3; 600/411, 412

(56) References Cited

U.S. PATENT DOCUMENTS

| 5,307,812 A | | 5/1994 | Hardy et al. |
| 5,443,068 A | | 8/1995 | Cline et al. |
| 5,485,839 A | * | 1/1996 | Aida et al. .................. 600/427 |
| 5,492,122 A | * | 2/1996 | Button et al. ............... 600/411 |
| 6,128,522 A | * | 10/2000 | Acker et al. ................ 600/411 |
| 2003/0036706 A1 | * | 2/2003 | Slayton et al. .............. 600/439 |

FOREIGN PATENT DOCUMENTS

| EP | 0627206 A2 | 12/1994 |
| EP | 0734742 A2 | 10/1996 |

* cited by examiner

Primary Examiner—Roy D. Gibson
(74) Attorney, Agent, or Firm—Blakely Sokoloff Taylor & Zafman

(57) ABSTRACT

A set for heat treatment of a target zone of a biological tissue, having an energy-generator to supply energy locally in the target zone, a mapper for measuring and recording temperature in the target zone, and a control unit to determine, on the basis of temperature measured in the target zone, the amount of energy required to be supplied to the target zone, and to control the energy-generator to deliver the energy. The control unit determines the energy required using point by point digital processing of the spatial distribution of temperature in the target zone and its immediate surroundings.

5 Claims, 9 Drawing Sheets

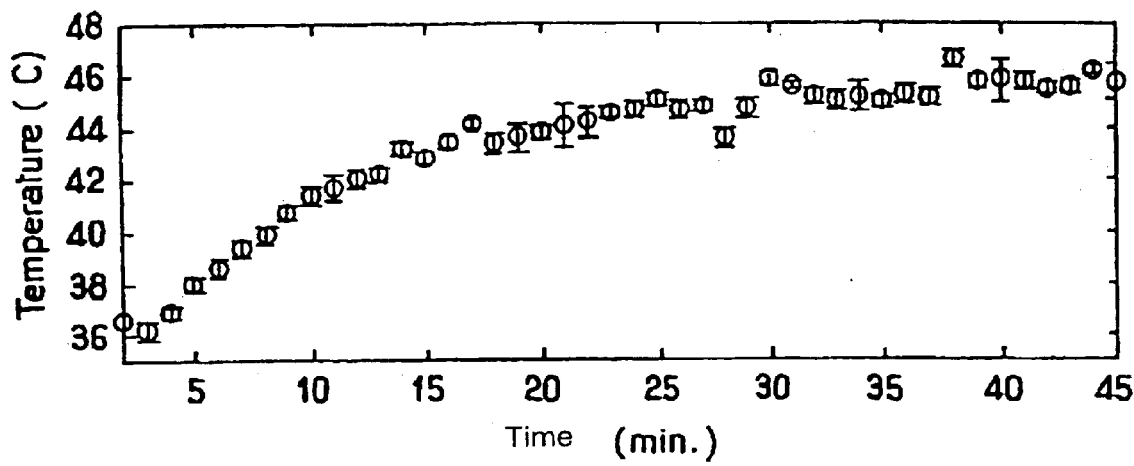
FIG_1
PRIOR ART
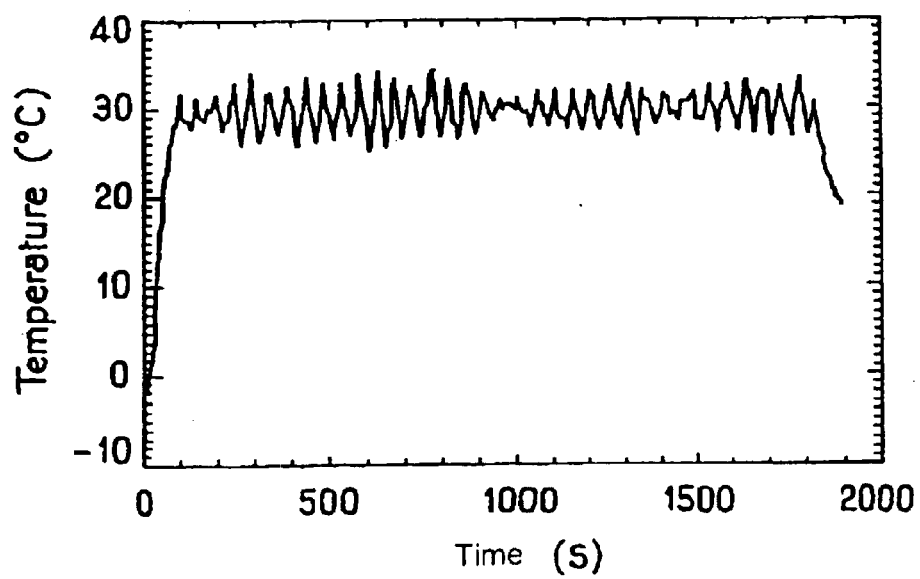
FIG_2
PRIOR ART

FIG_4

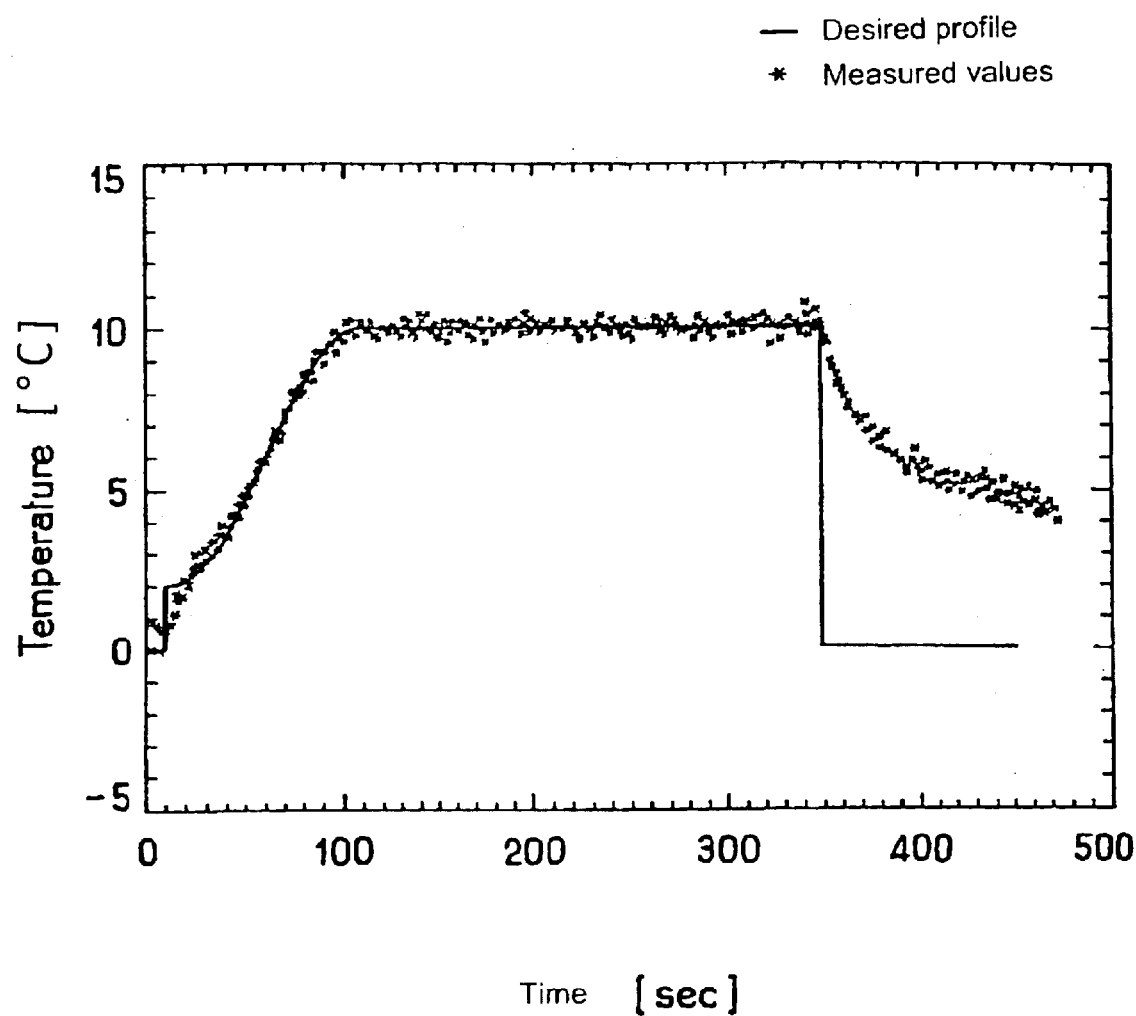
FIG_7

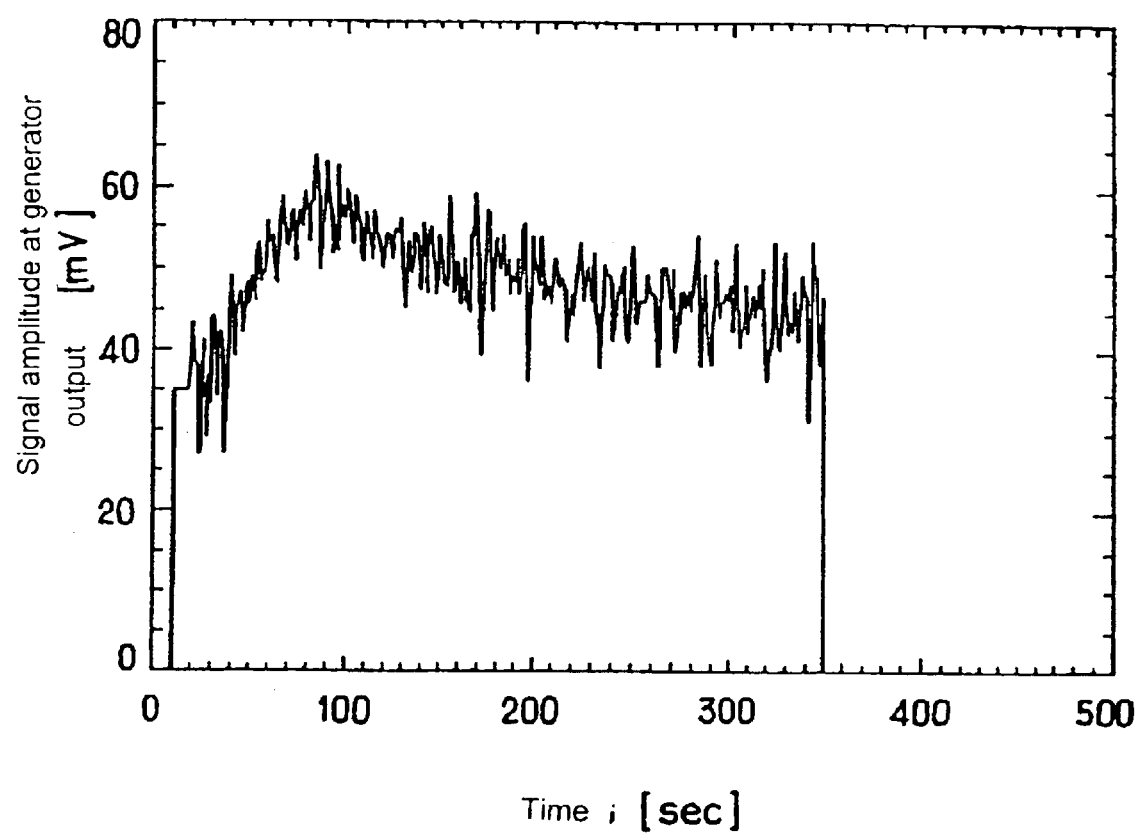
FIG_8

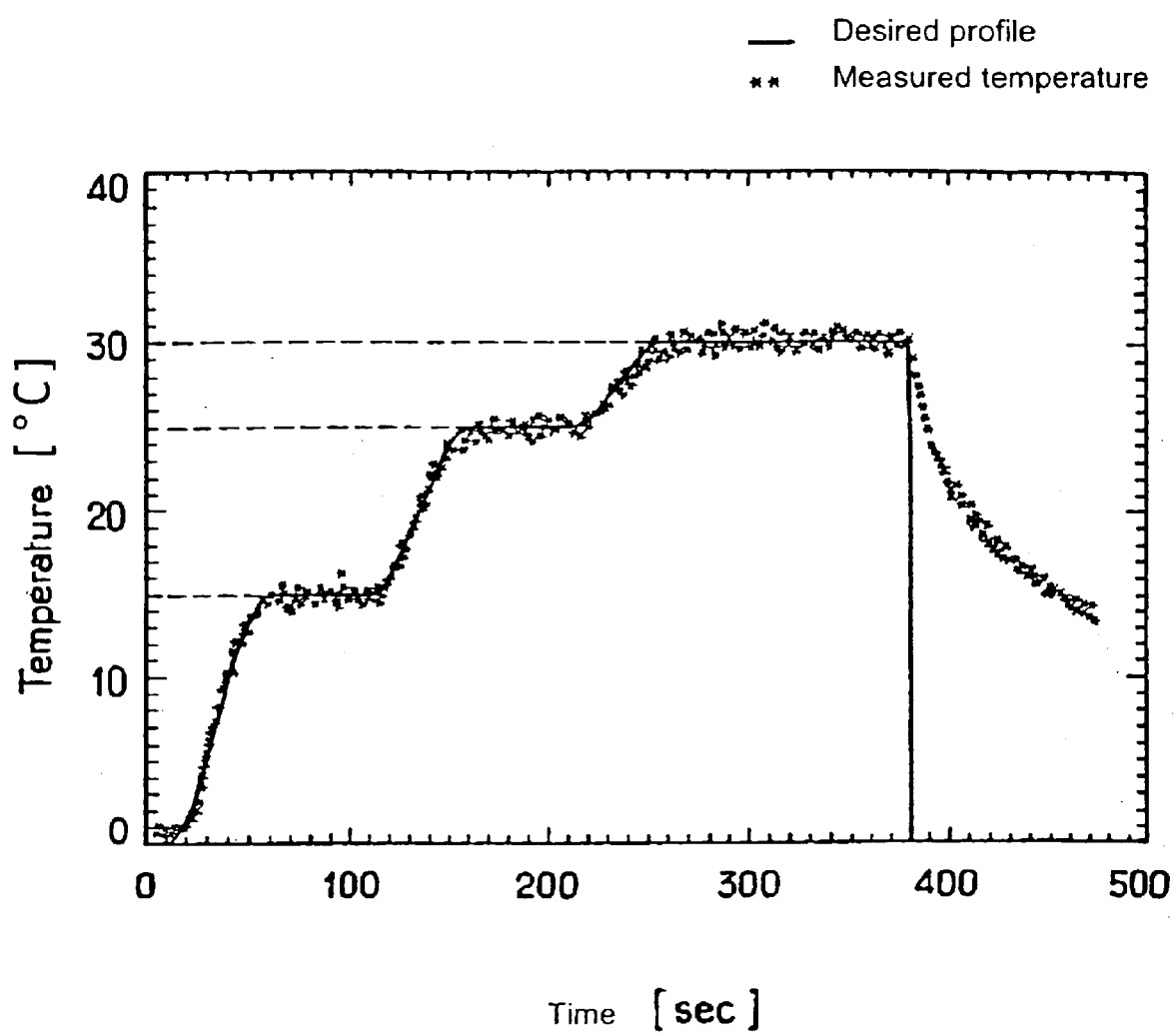
FIG_9

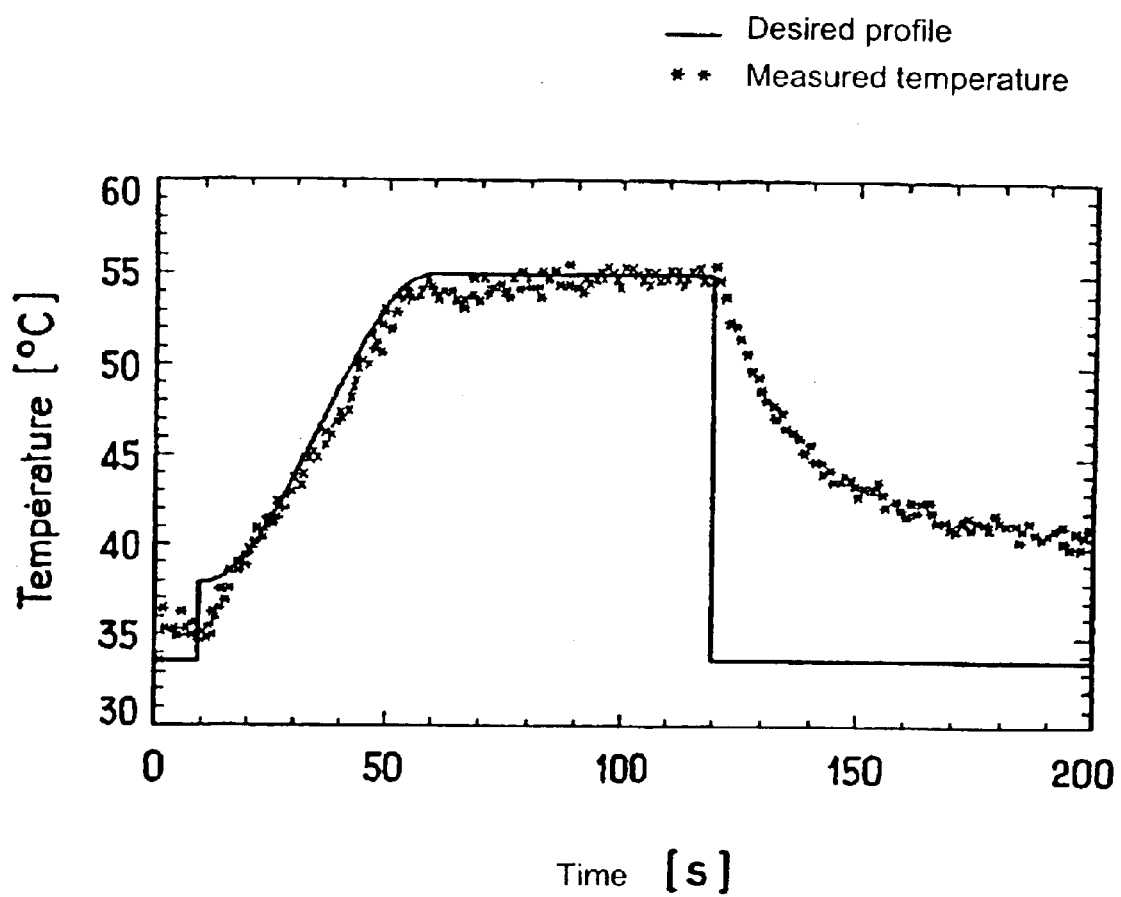
FIG_10

SET FOR HEAT TREATMENT OF BIOLOGICAL TISSUES AND METHOD USING SAME

BACKGROUND OF THE INVENTION (1) Field of the Invention

The invention relates to the field of apparatuses intended for local hyperthermia therapies. The invention also relates to a method of using apparatus of this sort.

(2) Description of Related Art

Local hyperthermia therapies consist in heating, locally, a target zone of biological tissue. When this type of therapy is used in the context of gene therapy, the heat may, for example, be used for its action on a heat-sensitive promoter. Heat may also be used to necrose biological tissue and to ablate tumors.

Also, local hyperthermia therapies offer numerous advantages. These advantages are both qualitative and economic. From the qualitative point of view, they offer, for example, strong potential for the control of treatments such as gene therapies, the local application of medications, the ablation of tumors, etc. From the economical point of view, they are compatible with the ambulatory treatment of patients, they make it possible to reduce the length of time spent in hospital, etc.

In hyperthermia therapies, the heat may, for example, be provided by a laser, microwaves or radio-frequency waves, focused ultrasound, etc. In general, local hyperthermia therapies allow medical operations where the invasive nature is reduced to the minimum. However, among the aforementioned energy types, focused ultrasound is particularly beneficial since it makes it possible to heat the focusing zone, in a noninvasive way, deep within a biological body, without significantly heating the tissue in the vicinity of the focusing zone.

In all cases, the temperature of the target zone and of its immediate surroundings, during the treatment, must be accurately and continuously controlled, although the supply of energy is localized and fast, of short duration (of the order of a few seconds). To this end, it is possible to fit temperature probes in the target zone and its immediate surroundings. However, it is also possible to use Magnetic Resonance Imaging (MRI). This is because MRI makes it possible to obtain an accurate map of the temperature distributions and detailed anatomical information. Furthermore, MRI allows noninvasive control of the temperature.

Devices for controlling the temperature during treatments by focused ultrasound are already known, based on magnetic resonance thermometry. Devices of this sort are in particular described in the following documents: "Control system for an MRI compatible intracavitary ultrasonic array for thermal treatment of prostate disease", Smith NB et al., Proceedings of the annual meeting of the International Society of Magnetic Resonance in Medicine, 1999, p. 672 and "Real time control of focused ultrasound heating based on rapid MR thermometry", Vimeaux FC et al., *Invest. Radiol.* 1999, 34, p. 190–193. In the devices described in these documents, the retrocontrol of the heat provided by the focused ultrasound, by virtue of the maps obtained by MRI, is of the PID (Proportional Integral and Derivative) type. Furthermore, with these devices, control of the heat supplied to the tissue is based on taking into account a temperature measured in the focusing zone of the ultrasound equipment, or corresponding to a mean obtained from the spatial temperature distribution in the mapped zone.

FIG. 1 shows the temporal change in the mean temperature of the focusing zone, processed by virtue of the device described in the first of these documents. In this figure, the temperature increases up to a plateau corresponding to the temperature that it is desired to reach in the focusing zone. It may be noted that the temperature desired in the focusing zone is reached only after a period of about 30 minutes.

FIG. 2 shows the temporal change in the mean temperature in the focusing zone, processed by virtue of the device described in the second of the documents mentioned above. It may be noticed that the temperature desired in the focusing zone is reached in less than 2 minutes. However, variations in the desired temperature, of plus or minus 4° C., are observed.

BRIEF SUMMARY OF THE INVENTION

One aim of the invention is to provide equipment for the heat treatment of a target zone of biological tissue, enabling the temperature desired in the target zone to be obtained quickly and at the same time the temperature in this target zone to be maintained and controlled with increased accuracy, compared to that which was possible with the techniques of the prior art.

This aim is achieved, according to the invention, by virtue of equipment for the heat treatment of a target zone of biological tissue, comprising:

energy generating means for supplying energy locally in the target zone;

means for measuring and recording the temperature in the target zone;

a control unit comprising means for determining, from the temperature measured in the target zone, the amount of energy having to be supplied to the target zone, and means for controlling the energy generating means to deliver this power value;

characterized in that the control unit furthermore comprises means of numerically processing, point by point, the spatial temperature distribution in the target zone and its surroundings, in order to calculate temperature gradients.

The heat treatment equipment according to the present invention takes into account the actual spatial temperature distribution in the target zone, but also in the surroundings of this zone. That is to say that it takes into account and processes, point by point, this spatial distribution. Unlike the heat treatment equipment of the prior art, the spatial temperature distribution is used to deduce therefrom temperature gradients and not merely averages. This makes it possible to estimate, with increased accuracy, the amount of energy which must be applied and therefore to achieve the desired temperature more quickly and to maintain the temperature of the biological tissue with greater stability.

Advantageously, the control unit of the heat treatment equipment according to the invention furthermore comprises means for estimating the local heat energy losses, from an estimate of the heat conduction and of the spatial temperature distribution in the target zone and its surroundings. This is because the information supplied by the value of the temperature gradients and the taking into account of an estimate of the local heat losses not only make it possible to understand the way in which the treated biological tissue has reacted to the heat already applied thereto, but furthermore, make it possible, by virtue of the prediction concerning the way in which the biological tissue will react to the heat. This also makes it possible to make the temperature of the heat-treated tissue change more quickly toward the desired temperature and to maintain the temperature of the biological tissue with greater stability.

Advantageously, the energy generating means of the heat treatment equipment according to the invention emit focused ultrasound. This is because focused ultrasound makes it possible to supply heat to a very localized zone, in a noninvasive manner, even if this zone is located deep within a human body or an animal. Furthermore, the focusing makes it possible for the tissue near to the zone of treated biological tissue not to be significantly heated.

Advantageously, the means for measuring and recording the spatial temperature distribution of the heat treatment equipment according to the invention comprise a magnetic resonance imaging apparatus. This is because MRI allows measurement of the temperature, which is noninvasive, accurate and well resolved in many points of the mapped zone. The data collected by MRI are, furthermore, easily processed numerically.

Advantageously, the heat treatment equipment according to the invention comprises means for evaluating the spatial distribution, in the target zone and its surroundings, of the energy supplied to the target zone.

According to another aspect, the invention is a method for regulating equipment for heat treating a target zone of biological tissue, comprising the step consisting in locally applying energy to the target zone, characterized in that it further comprises the steps consisting in evaluating the temperature gradients in the target zone and its surroundings; and thereby deducing the energy to be applied to the target zone in order to reach the desired temperature.

Advantageously, this method furthermore then comprises the step consisting of estimating the local energy losses, in the target zone and its surroundings.

Advantageously, this method furthermore comprises the step consisting of evaluating the spatial distribution, in the target zone and its surroundings, of the energy supplied to the target zone.

Other aspects, aims and advantages of the invention will become more clearly apparent on reading the following detailed description.

BRIEF DESCRIPTION OF THE SEVERAL VIEWS OF THE DRAWINGS

The invention will also be better understood by means of the appended drawings in which:

FIG. 1 shows the temporal change in temperature of a target zone, when the target zone is treated using heat treatment equipment of the prior art;

FIG. 2 shows the temporal change in temperature of a target zone treated by another heat treatment equipment of the prior art;

FIG. 7 shows the temporal change in the maximum temperature, measured during the thermal treatment of biological tissue, by the equipment according to the present invention, corresponding to the same in vitro experiment as that of FIG. 5;

FIG. 8 shows the temporal change in the amplitude of the signal emitted by the generator of the equipment according to the present invention, during the thermal treatment of a biological tissue, corresponding to the same in vitro experiment as that in FIGS. 5 and 7;

FIG. 9 shows the temporal change in the maximum temperature, during the heat treatment, of a biological tissue, by the equipment according to the present invention, corresponding to another in vitro experiment, with three temperature stages, and described below; and FIG. 10 shows the temporal change in the maximum temperature, measured during the heat treatment by the equipment according to the present invention, corresponding to an in vivo experiment described below.

DETAILED DESCRIPTION OF THE INVENTION

One of the embodiments of the invention is described below in detail. By way of example, this embodiment of the invention corresponds to equipment for local hyperthermia treatment by focused ultrasound, controlled by MRI.

Figure 3:
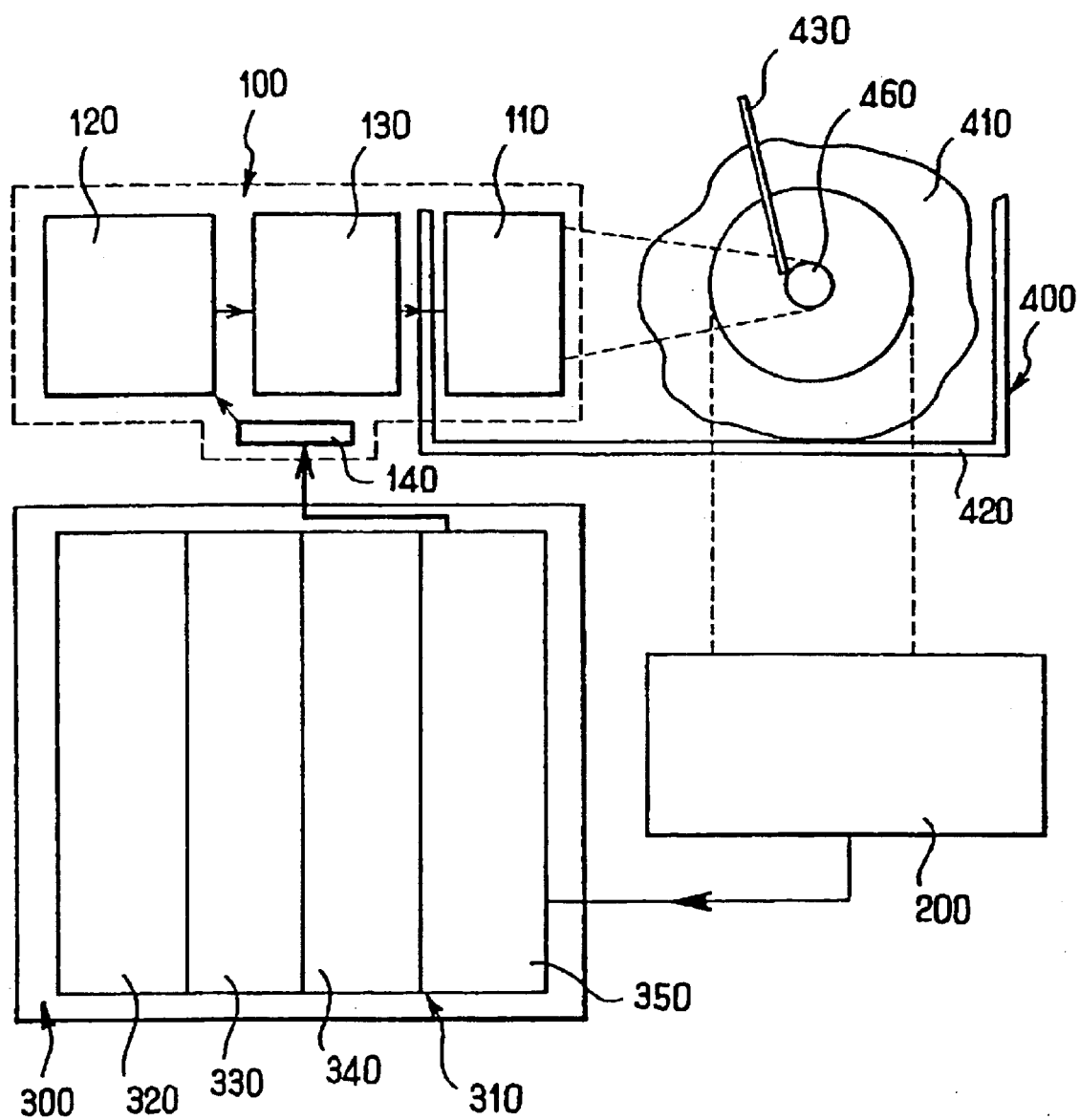
FIG. 3 shows schematically the heat treatment equipment according to the invention.

As shown in FIG. 3, equipment of this sort comprises:

energy generating means 100;

mapping means 200;

a control unit 300; and a sample holder 400 for the biological tissue 410 to be treated.

In the embodiment of the invention described here, the energy generating means 100 consist of a transducer 110, a sinusoidal signal generator 120, an amplifier 130 and a converter 140, connecting the sinusoidal signal generator 120 to the control unit 300.

The transducer 110 operates at 1.45 MHz. A transducer 110 of this type is, for example, marketed by Speciality Engineering Associates® (Soquel, Calif.). Its diameter and its focal length are 38 mm and 25 mm, respectively.

The sinusoidal signal generator 120 is, for example, of the FG110 type, marketed by Yokogawa® (Tokyo, Japan).

The amplifier 130 is, for example, of the KMP 170F type, marketed by Kalmus® (Bothell, Wash.). This amplifier 130 has a power gain of 58 dB.

The converter 140 is, for example, a series IEEE488 converter, marketed by I. O. Tech.® (Cleveland, Ohio).

The mapping means 200 make it possible to measure and record the spatial temperature distribution. They comprise, for example, an MRI apparatus of the Bruker Biospec type marketed by Bruker® (Ettlingen, Germany). This apparatus uses a 4.7 T magnet which is equipped with a 120 mm diameter insert, which generates magnetic field gradients (the maximum value of the gradient is 0.193 T/m).

The control unit 300 comprises, in particular, a work station 310 of the Alpha PW 500a MHz type, marketed by Digital®.

The control unit 300 also comprises means for evaluating and numerically processing the spatial temperature distribution 320, means for determining the power value 330 having to be supplied to the target zone, means for estimating local losses of heat energy 340 and means 350 for controlling energy generating means 100. The control means 350 instruct the energy generating means 100 to deliver the power value supplied by the means 330 for determining the power value.

The sample holder 400 comprises a rat support 420, made of plexiglas®. This support 420 contains the transducer 110 and a surface coil (not shown in FIG. 3). A sample holder 400 of this type has already been described in the documents "Fast lipid suppressed MR temperature mapping with echo-shifted gradient echo imaging and spectral-spatial excitation", by Zwart JA et al., 1999, Magn. Res.Med., 42, p. 53–59; and "On the feasibility of MRI-guided focused ultrasound for local induction of gene expression", Madio DP et al., 1998, J. Magn. Res. Imaging. I, 8, p. 101–104. The support 420 is placed in the plexiglas® tube which is partly filled with water. The transducer 110 is positioned so that the focusing point 460 of the ultrasound is located approximately 10 mm deep within the biological tissue 410. During the in vitro measurements, a temperature probe 430 is inserted into the biological tissue 410 consisting of a piece of fresh meat, so as to have a temperature reference. This probe 430 is, for example, a thermocouple of the Digi-Sence DualLog type, marketed by Cole-Parmer Instrument Co.® (Vernon Hill, Ill.).

The preparation of the samples for the in vitro and in vivo experiments is carried out as follows. Male rats of the Wistar race from 325 to 500 g are taken. The latter are anesthetized by combining 1% by volume of halothane with a mixture consisting of 7 volumes of nitrous oxide ($N_2O$) to 3 volumes of oxygen, according to an approved protocol. In order to improve the penetration of the ultrasound beam into the biological tissue 410, the thigh of the rat (which is between the transducer and focal point) is depilated, using a product provided to this end and known to a person skilled in the art. During the in vivo measurements, the endorectal temperature of the rats is recorded. The body temperature of the rats is maintained at 35° C. by immersion of the bodies of the rats in a bath, the temperature of which is regulated for this purpose. After the heat treatment, the rats are sacrificed.

The mapping means 200 are used by implementing an Echo gradient sequence, with the following parameters: TR=50 ms, TE=15 ms, matrix size=64×63, three k lines per TR, FOV=64 mm×63 mm, where TR is the repetition time, TE is the echo time and FOV is the field of view. The data are obtained by MRI, from a section 2 mm in thickness, perpendicular to the ultrasound transducer and comprising the focal point of the focused ultrasound. The temporal resolution of the maps obtained by MRI is 1.05 s. The spatial resolution of the maps obtained by MRI is 1×1×2 mm³. The maps of the temperature measured by magnetic resonance are obtained from measurements of the shift in the water proton frequency. The choice of the water proton resonance, in order to carry out these measurements, is based on the fact that the relationship between the water proton resonance frequency and the temperature is, to a first approximation, independent of the composition of the biological tissue 410. The shift in the water proton frequency as a function of the temperature is, furthermore, linear and this linearity is not affected by the modifications of the biological tissue 410 induced by heat (Ishihara Y et al., Magn. Res. Med., 1995, 34, p. 814–823; Peters RD et al., Magn. Res. Med., 1998, 40, p. 454–459). The temperature dependence of the proton resonance frequency is 0.0094 ppm—$K^{-1}$ ("*Fast magnetic-resonance temperature imaging*"; by Zwart JA et al, 1996, J. Mag. Res. B, 112, p 86–90; "*Fast lipid suppressed MR temperature mapping with echo-shifted gradient echo imaging and spectral-spatial excitation*", by Zwart JA et al., 1999, Magn. Res. Med., 42, p. 53–59).

The magnetic resonance signals coming from lipids constitute a significant error source in the calculated temperature maps, since the resonance frequencies of the protons of the lipids do not depend on the temperature. The magnetic resonance signals coming from the lipids are therefore removed, by using selective excitation of water, in the manner described in the document "*Fast lipid suppressed MR temperature mapping with echo-shifted gradient echo imaging and spectral-spatial excitation*", by Zwart JA et al., 1999, Magn. Res. Med., 42, p. 53–59.

The use of means for evaluating and numerically processing the spatial temperature distribution 320 has also already been described in the document "*Fast lipid suppressed MR temperature mapping with echo-shifted gradient echo imaging and spectral-spatial excitation*", by Zwart JA et al., 1999, Magn. Res. Med., 42, p. 53–59.

One implementational example of the method for regulating the heat treatment equipment, according to the present invention, is described in detail below.

Figure 4:
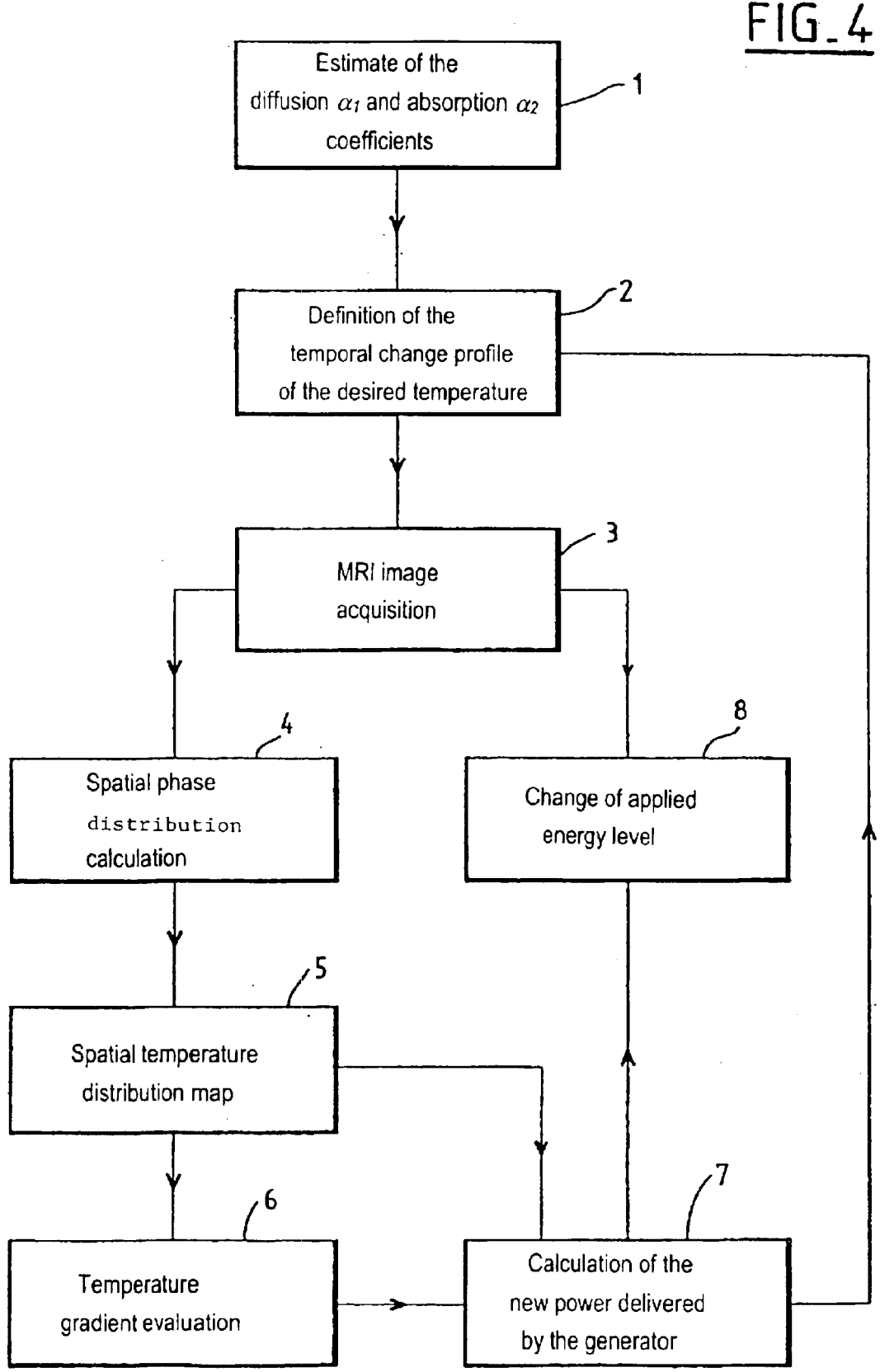
FIG. 4 is a flow diagram of the regulation method according to the present invention.

FIG. 4 shows schematically a flow diagram of this particular mode of implementing the method according to the invention.

According to this implementational example, the method according to the invention comprises:

a step 1 for estimating the heat diffusion coefficient ($\alpha_1$) and the absorption coefficient ($\alpha_2$) of the focused ultrasound in the biological tissue 410;

a step 2 for defining by the user, a temporal change profile of the desired temperature;

a step 3 for acquiring an MRI image;

a step 4 for calculating the spatial distribution of the phase at the focal point 460 and in its surroundings;

a step 5 for establishing the spatial temperature distribution at the focal point 460 and its surroundings;

a step 6 for evaluating the temperature gradients of the focal point 460 and in its surroundings;

a step 7 for determining the new power having to be delivered by the generator 120; and a step 8 for changing the energy level applied by the generator 120.

Steps 3 to 8 are carried out in a loop, in order to reach and to follow the temporal change profile of the desired temperature, defined in step 2.

For a given element of the transducer 110, the electrical power P(t) transmitted to a sample is determined by the means for determining the power value 320. Its value may therefore be altered directly by the control unit 300. It is obtained on the basis of the equation:

$$P(t) = \frac{1}{\alpha_2(T_{max})}\left[\frac{d\Theta(t)}{dt} - \alpha_1(T_{max}) \cdot \nabla^2 T_{max}(t) + \alpha \cdot [\Theta(t) - T_{max}(t)] + \frac{\alpha^2}{4} \cdot \Delta(t)\right]$$

This equation is established by considering the following.

The focal point is defined by $\vec{r} = (0,0,0)$. The temporal change and the maximum temperature of the focal point then corresponds to $T_{max}(t) = T(0,0,0,t)$. Let us denote the predetermined profile of the desired temporal change in the maximum temperature $T_{max}(t)$ by $\Theta(t)$. As indicated above, this profile is defined before the start of each experiment. For example, this profile $\Theta(t)$ comprises a rise of 10° C. over 100 s. This rise step follows the change of a half period of the cosine function. It is followed by a period where the temperature is constant (10° C. above the starting value), for 250 s.

The maximum temperature $T_{max}(t) = T(0,0,0,t)$ may be controlled only at the focal point. This is because the geometry of the transducer 110 and the spatial distribution of the refractive index in the biological tissue 410 determines the acoustic field. Consequently, the temperature change other than in the focusing zone involves functions dependent on the space coordinate $\vec{r}$ and on the temperature T. The acoustic power field $\rho(\vec{r})$, the heat diffusivity tensor $\hat{\alpha}_1(\vec{r},T)$ in the biological tissue 410 and the absorption coefficient $\alpha_2(\vec{r},T)$ for the focused ultrasound are then related by the equation:

$$\frac{\partial T(\vec{r}, t)}{\partial t} = \vec{\nabla}[\hat{\alpha}_1(\vec{r}, T) \cdot \nabla T(\vec{r}, t)] + \alpha_2(\vec{r}, T) \cdot \rho(\vec{r}) \cdot P(t). \quad [1a]$$

When the diffusivity is isotropic and varies slowly in space, equation 1a is simplified to give the equation 1b, where $$\alpha_1(\vec{r}, T) = \frac{1}{3} Tr[\hat{\alpha}_1(\vec{r}, T)]$$

is a scalar field and $\nabla^2$ is the Laplacian operator defined by $$\frac{\partial^2}{\partial x^2} + \frac{\partial^2}{\partial y^2} + \frac{\partial^2}{\partial z^2};$$

$$\frac{\partial T(\vec{r}, t)}{\partial t} = \alpha_1(\vec{r}, T) \cdot \nabla^2 T(\vec{r}, t) + \alpha_2(\vec{r}, T) \cdot \rho(\vec{r}) \cdot P(t) \quad [1b]$$

It should be noted that the functions $\alpha_1(\vec{r},T)$ and $\alpha_2(\vec{r},T)$ are not accurately known at the start of heating.

The acoustic power field of a spherical element of a focused ultrasound transducer corresponds approximately to a Gaussian distribution about the focal point 460, with an attenuation radius at 6 dB denoted $R_0$. The specific diffusion time $\tau$ is defined by $$\tau = \frac{R_0^2}{2\alpha_1}.$$

For an ultrasonic wavelength of 1 mm, the order of magnitude of $\tau$ is about 10 s.

The following objectives are established:
1) the temperature of the focal point 460 must reach the desired temperature as quickly as possible (that is to say in a time of the same order of magnitude as $\tau$), this without oscillating or exceeding the desired value;
2) once this desired value is reached, the temperature must remain constant for a period predefined by the user.

The integral of the profile $\Theta(t)$, the integral of the time change of the maximum temperature of the $T_{max}$ (t) observed experimentally and the difference between these two integrals, are respectively:

$$\Omega(t) = \int_0^t \Theta(t')dt' \quad [2a]$$

$$\Psi(t) = \int_0^t T_{max}(t')dt \quad [2b]$$

$$\Delta(t) = \Omega(t) - \Psi(t) = \int_0^t [\Theta(t) - T_{max}(t')]dt \quad [2c]$$

By using these expressions, equation 1b, giving the temperature change at the focal point, can be expressed as a function of $\Delta(t)$:

$$\frac{d^2\Delta(t)}{dt^2} = \frac{d\Theta(t)}{dt} - \alpha_1(T_{max}) \cdot \nabla^2 T_{max}(t) - \alpha_2(T_{max}) \cdot P(t) \quad [3]$$

where $\vec{r} = (0,0,0)$ is omitted and $\rho(0,0,0)=1$.

In equation 3, the parameter which it is desired to control directly is the power $P(t)$ of the focused ultrasound. Let us note that a second order differential equation which is linear in $\Delta(t)$, can be advantageously used by the control unit 300, in a way similar to a PID control system. The reason for this is that the solution for $\Delta(t)$ of such an equation tends asymptotically toward zero, and that this is the same for its first derivative. If the first derivative of $\Delta(t)$ is equal to zero, $T_{max}(t)$ overlaps with the predetermined profile of the temporal change in the temperature $\Theta(t)$. This constitutes the fundamental idea of the control method implemented by the control unit 300. Thus, we can rewrite equation 3 in the form of a linear differential equation of second order in $\Delta(t)$ of the type:

$$\frac{d^2\Delta}{dt^2} + \alpha \cdot \frac{d\Delta}{dt} + \frac{\alpha^2}{4} \cdot \Delta = 0 \quad [4]$$

So as to obtain the expression wanted for equation 4 from equation 3, $P(t)$ is rewritten with the following expression:

$$P(t) = \frac{1}{\alpha_2(T_{max})} \left[ \frac{d\Theta(t)}{dt} - \alpha_1(T_{max}) \cdot \nabla^2 T_{max}(t) + \alpha \cdot [\Theta(t) - T_{max}(t)] + \frac{\alpha^2}{4} \cdot \Delta(t) \right] \quad [5]$$

Equation 5 corresponds to the central equation used to calculate directly the power level of the focused ultrasound. From the solution of the second order differential equation, corresponding to equation 4, it is possible to see that the parameter a is connected to the characteristic response time $t_r$ of the regulation loop, by the expression $a=2/t_r$. It is supposed that in the equations 4 and 5, all the functions used to calculate the power $P(t)$ are accurately known. It is also possible to verify, as shown by equation 6 below, that the temperature $T(t)$, observed experimentally, tends asymptotically toward the profile $\Theta(t)$:

$$\Theta(t) - T(t) = \frac{d\Delta}{dt}(t) = [\Theta(0) - T(0)] \cdot \left(1 - \frac{\alpha}{2} \cdot t\right) \cdot \exp\left(-\frac{\alpha}{2} \cdot t\right) \quad [6]$$

As already noted above, in an actual experiment, the ultrasound absorption coefficients $\alpha_2$ and the heat diffusion parameter $\alpha_1$, and their temperature dependence, are unknown. These parameters $\alpha_1$ and $\alpha_2$ depend on the composition of the biological tissue 410, on physiological processes, such as perfusion, and on irreversible changes taking place during the heating procedure, for example in the ablation procedures. Thus, a regulation system must be tolerant to errors on the parameters $\alpha_1$ and $\alpha_2$.

Only the profile $\Theta(t)$ and its derivative are accurately known.

Thus, when the ultrasonic power is calculated directly from equation 5, two difficulties become apparent:
1) $T_{max}(t)$ and $\nabla^2 T_{max}(t)$ as are obtained from the temperature mapping arising from the MRI, are affected by the noise.
2) the values of $\alpha_1$ and $\alpha_2$ and their temperature dependentce are not accurately known, similarly, their sensitivity to necrosis by heating (for example in the ablation procedures) and the physiological parameters such as perfusion, are not accurately known.

Any error which may affect $\alpha_1$ and $\alpha_2$ may be treated as a parameter error in a control loop, according to a linear model. Thus, estimates of the initial values of $\alpha_1$ and $\alpha_2$ will be chosen, then used during the heating procedure, in order to calculate the ultrasonic power, according to equation 5.

Theoretical analysis of the effect of the error on the parameters $\alpha_1$ and $\alpha_2$ in equation 5 highlights the following effects:

1) an incorrect estimate of the parameter $\alpha_2$ decreases the efficiency of the regulation loop; the possibility of exceeding the desired temperature or too small a value of the determined temperature may in fact ensue; this then has the consequence of increasing the convergence time. Whatever the case, even in these conditions, the experimental temperature always tends asymptotically toward the predetermined profile of the temporal change in temperature.
2) an incorrect estimate of the parameter $\alpha_1$ leads to a constant offset, in the zone where the profile $\Theta(t)$ is flat, of the temperature values, between the temperature values measured experimentally and the profile $\Theta(t)$. This offset is proportional to the first derivative, with respect to time, of the Laplacian, multiplied by the absolute error in $\alpha_1$, times $a^{-2}$. In order to estimate this effect, the derivative of the Laplacian has been determined by using linear regression of the curve shown in FIG. 5, between 150 and 250 s. Its value is about 0.01 $K.mm^{-2}.s^{-1}$, which leads to a temperature offset of approximately 0.1° C. Thus, the error in the actual temperature should not be directly observed because of the limitation in the accuracy of the thermometric measurements by magnetic resonance, because of the noise.

The influence of the error in the values $\alpha_1$ and $\alpha_2$ on the efficiency of the temperature control by the heat treatment equipment according to the invention is studied experimentally, on a piece of fresh meat, below.

According to step 1, the parameters $\alpha_1$ and $\alpha_2$ must be estimated. This is carried out, firstly from a preliminary experiment with a constantly focused ultrasonic power. The parameter $\alpha_1$ is calculated from the derivative, with respect to time, of the temperature at the focal point, divided by the mean (over five MRI images) of the Laplacian. It is calculated immediately after extinction of the focused ultrasound emission and is expressed in $mm^2/s$. The parameter $\alpha_2$ (the rate at which energy is applied to the focal point taking into account the spatial power distribution of the focused ultrasound) is calculated from the derivative, at the initial time, of the temperature of the focal point, with respect to the power of the focused ultrasound (when the focused ultrasound is emitted and the diffusion is negligible, see equation 1). It is expressed in $K.s^{-1}.(mV)^{-2}$. The accuracy estimated for $\alpha_1$ and $\alpha_2$ is better than 10%, as may be deduced from repeated experiments. The numerical values obtained in this way may be directly used in equation 5 in order to calculate, each time a new temperature map is available, the actual value of the power having to be supplied by the generator 120.

According to step 2, a profile of the desired temporal change in the temperature at the focal point is defined before the start of each experiment. This profile comprises an increasing initial part, corresponding to a half period of the cosine function, followed by a constant temperature part. The first derivative of the curve corresponding to this profile is continuous and may be calculated numerically by computer.

Step 3 is implemented by virtue of the mapping means 200.

Steps 4 to 6 are implemented by virtue of the evaluation means for numerically processing the spatial temperature distribution 320. The phases are calculated from the MRI signals, obtained by virtue of the mapping means 200. The changes in the water resonance frequency are calculated from these phases. The temperature changes are calculated from these frequency changes.

The maximum temperature $T_{max}(t)$ and the integral $\Delta(t)$ are directly deduced from the mapping obtained by MRI, respectively during steps 5 and 6. The integral $\Delta(t)$ (equation 2c) is calculated numerically using the work station 310.

During step 6, the local heat energy losses are re-evaluated using means for estimating local heat energy losses 340.

According to step 7 of the method according to the present invention, the Laplacian operator $\nabla^2 T(\vec{r},t)$ is applied to processing the temperature maps obtained by MRI. The value of this Laplacian at the focal point is calculated, using the finite element method, in combination with a temporal noise reduction filter. This filter uses a binomial weighting ratio of 1:4:6:4:1, over five images. This step 7 is implemented with the means 330 for determining the power value.

Finally, the power is calculated by virtue of equation 5 and the value calculated is sent to the converter 140 (step 8). Step 8 is implemented with the means 350 for controlling the energy generating means 100.

The total calculation duration for processing each spatial temperature distribution map, that is to say each cycle of the set of steps 3 to 8 described hereinabove, is less than 250 ms.

Figure 6:
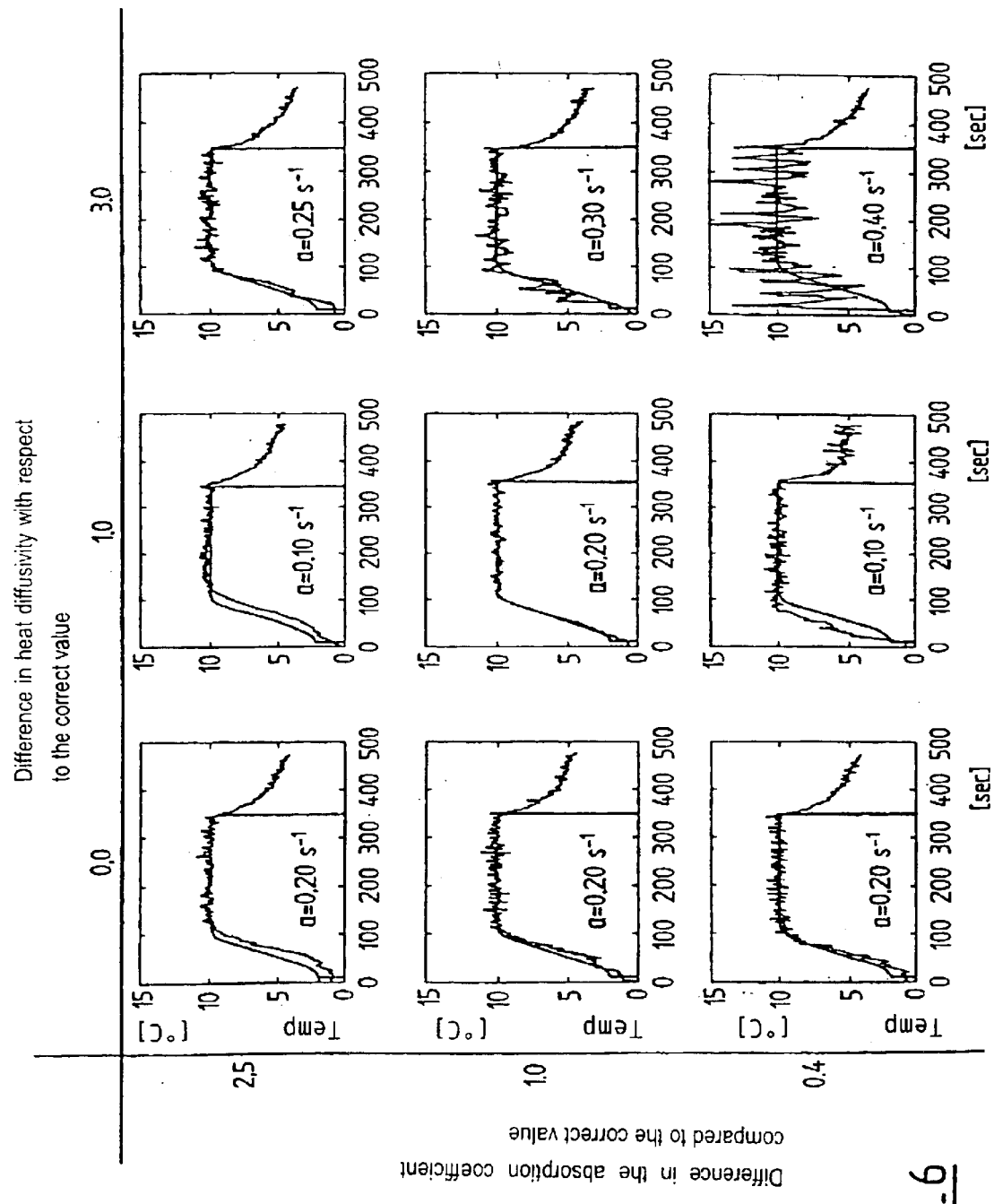
FIG. 6 shows the results of a series of experiments aiming to examine the effect of estimation errors on the energy losses, represented by the heat diffusivity and the absorption coefficient of the ultrasonic energy.

To analyze the tolerance with respect to errors in the initial estimates of $\alpha_1$ and $\alpha_2$, several heating procedures have been implemented with the parameters $\alpha_1$ and $\alpha_2$ varying over a large range. This range goes from 0 to 300% of a predetermined value, for $\alpha_1$, and from 40 to 250%, for $\alpha_2$. This predetermined value is that obtained from preliminary measurements outlined above. Waiting times of 30 minutes have been introduced between successive experiments with the aim of reaching the temperature base lines which are spatially uniform in the sample and identical for each experiment. Nine representative results are recorded in FIG. 6. These results show that the system has a large tolerance with respect to errors in the estimates of the initial values of $\alpha_1$ and $\alpha_2$. Be that as it may, it is possible to note that the control loop becomes unstable only when $\alpha_1$ is heavily overestimated. This instability is exacerbated when $\alpha_1$ is heavily overestimated and $\alpha_2$ is underestimated. This effect may be attributed to the experimental noise of the temperature measurements by MRI. When a calculation affected by the noise leads to an overestimate in the value of the Laplacian (the second derivatives being sensitive to the noise), the power of the focused ultrasound applied increases in a ratio equal to $\alpha_1.\epsilon/\alpha_2$, where $\epsilon$ is the overestimate of the Laplacian. An increase in the power of the focused ultrasound leads to a strong increase in the Laplacian in the biological tissue 410 and, as a result, a new increase in the power of the focused ultrasound. This positive reaction will cease after a time approximately equal to $2/a$, by virtue of a negative reaction in the control loop. This explains the periodicity of the instability in this extreme case.

The strength of the negative reaction on the regulation loop corresponds to the parameter a. This is because, as we have seen above, the parameter a is equal to twice the inverse of the characteristic response time $t_r(a=2/t_r)$. The value of this parameter is indicated for each example of FIG.

6. In general, the values of a of $0.1\ s^{-1}$ to $0.2\ s^{-1}$ are enough to reach temperature rise times similar to those of the profile $\Theta(t)$, even when extremely incorrect values of $\alpha_1$ and $\alpha_2$ are used. It is only in the extreme case where $\alpha_1$ is heavily underestimated and $\alpha_2$ is overestimated (see FIG. 6, at the bottom right), that a must be increased up to the value of $0.40\ s^{-1}$ in order to obtain an overlap with the predetermined profile of the temporal change of the temperature. The optimum value of a, found experimentally (in all cases, except the cases with extreme errors in $\alpha_1$ and $\alpha_2$), is $0.2\ s^{-1}$, the response time of the corresponding regulation loop being 10 s. When the strength of the negative reaction is increased, a faster correction of the errors in the initial parameters is obtained, but the amplitude of the power of the focused ultrasound and of the temperature fluctuations around the predetermined value is also increased.

The implementation and the performance of the treatment equipment according to the invention described above are illustrated below by means of two examples.

Figure 5:
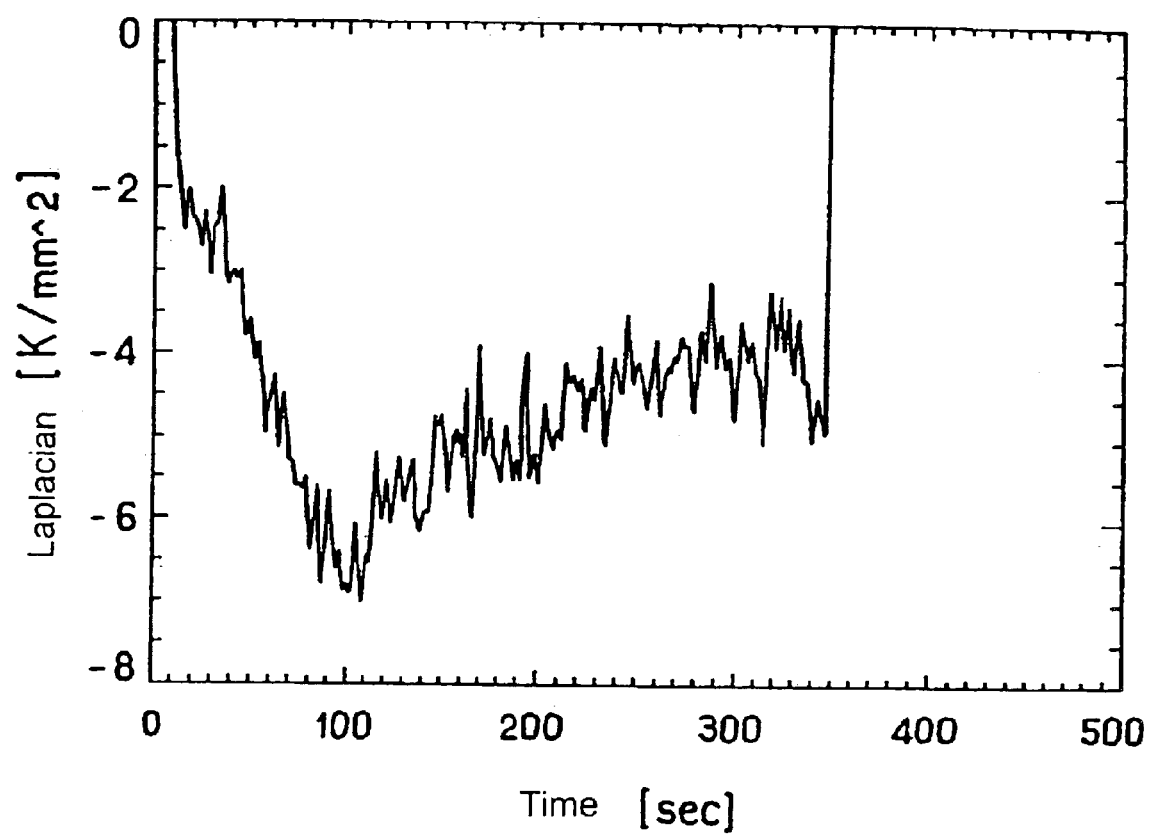
FIG. 5 shows the temporal change in the Laplacian type, during heat treatment by the equipment according to the present invention, corresponding to an in vitro experiment described below.

Example 1: Use of the heat treatment equipment, according to the present invention, in the context of in vitro measurements According to this example, a temperature rise protocol of 10° C. is implemented on a sample of fresh meat. The initial temperature is equal to 15° C. With this protocol, no irreversible alteration of the biological tissue 410, resulting from this temporal change profile of the temperature, is expected. FIG. 7 shows the change in the maximum temperature as a function of time. In the flat part of this curve, the mean temperature rise is 9.97° C., with a standard deviation of 0.19° C. This standard deviation must be compared with that, equal to 0.18° C., which is obtained by the temperature measurements carried out without heating by focused ultrasound (that is to say that which corresponds to the base line of noise in the temperature measurements). FIG. 5 shows the directly calculated Laplacian. The attenuation observed over the constant temperature part corresponds to the decrease in temperature gradients around the focal point. As for the amplitude of the directly applied power, this is shown in FIG. 8. Because of the measurement noise, the calculated value of the Laplacian and the amplitude of the power supplied by the generator have a fluctuation of about 10%, approximately. This has only a small effect on the resulting temperature, since the fluctuation frequency (that is to say the inverse of the temporal resolution of the map by magnetic resonance) is much greater than the inverse of the response time ($\tau$) specific to the heating of the biological tissue 410.

FIG. 9 shows the temperature stability obtained with a profile having three stages (15, 25, 30° C.). The standard deviation is 0.35° C., 0.36° C. and 0.40° C., respectively, for temperature rises to 15° C., 25° C. and 30° C. Results shown in FIG. 9 confirm the high temperature stability over a large range of temperature increase, of the system for regulating the heat treatment equipment according to the present invention.

Example 2: Use of the heat treatment equipment, according to the present invention, in the context of in vivo measurements By adopting a procedure similar to that implemented in the case of example 1, experiments were carried out in vivo, on a rat's thigh. The corresponding results are shown in FIG. 10. The temporal resolution is 0.5 s. The mean temperature, between 90 and 120 s after the start of the experiment, is 54.9° C. (the value of the profile to be reached is 55° C.) with a standard deviation of 0.33° C. FIGS. 7, 9 and 10 show that it is possible to control the temperature with an accuracy close to that given by the temperature measurements carried out in vitro or in vivo.

An embodiment of the invention corresponding to local hyperthermia treatment equipment by focused ultrasound, controlled by MRI, has been described above, but the invention covers a much wider range of heat treatment equipment. Also, it will be understood that the invention may be generalized to the cases where the heat is, for example, provided by a laser, microwaves or radiofrequency waves, focused ultrasound, etc. It will also be understood that other means of measuring the temperature may be used in the heat treatment equipment according to the present invention, in the place of MRI.

Similarly, the evaluation and numerical processing of the spatial temperature distribution have been described above as being carried out using the Laplacian. Other means of carrying out this evaluation may be used without departing from the scope of the invention.

What is claimed is:

1. Equipment for the heat treatment of a target zone of biological tissue, comprising:

energy generating means for supplying energy locally in the target zone;

means for measuring and recording a temperature in the target zone;

a control unit comprising means for determining, from the temperature measured in the target zone, an amount of energy having to be supplied to the target zone necessary to reach and maintain a desired temperature in the target zone, and means for controlling the energy generating means to deliver the amount of energy having to be supplied;

the control unit further comprising means for numerically processing, point by point, a spatial temperature distribution in the target zone and its surroundings, in order to calculate temperature gradients.

2. The equipment as claimed in claim 1, wherein the control unit further comprises means for estimating local heat energy loses, from an estimate of the heat conduction and of the spatial temperature distribution in the target zone and its surroundings.

3. The equipment as claimed in claim 1, wherein the energy generating means emits focused ultrasound.

4. The equipment as claimed in claim 1, wherein the means for measuring and recording the spatial temperature distribution further comprise a magnetic resonance imaging apparatus.

5. The equipment as claimed in claim 1, 2, 3 or 4 further comprising means for evaluating the spatial distribution, in the target zone and its surroundings, of the amount of energy having to be supplied to the target zone.

* * * * *